United States Patent [19]

Heller et al.

[11] Patent Number: 5,312,594
[45] Date of Patent: May 17, 1994

[54] SEWAGE TREATMENT APPARATUS

[75] Inventors: Jon D. Heller, Denver; Kenneth J. Heller, Englewood; Timothy Reeves, Arvada, all of Colo.

[73] Assignee: Nutech Environmental Corp., Denver, Colo.

[21] Appl. No.: 947,301

[22] Filed: Sep. 18, 1992

[51] Int. Cl.⁵ .................................................. G05D 9/00
[52] U.S. Cl. .................................. 422/106; 422/111; 210/104; 210/206; 141/95
[58] Field of Search ................. 422/5, 111, 106; 210/104, 105, 206, 207, 758, 749, 702, 723; 141/94-95, 198

[56] References Cited

U.S. PATENT DOCUMENTS

| | | | |
|---|---|---|---|
| 3,266,224 | 8/1966 | Ferretti | 55/241 |
| 3,625,491 | 12/1971 | Yokoi et al. | 261/23 |
| 3,920,550 | 11/1975 | Farrell, Jr. et al. | 210/104 |
| 3,937,662 | 2/1976 | Bartik | 210/104 |
| 4,225,566 | 9/1980 | deVries | 423/210 |
| 4,226,714 | 10/1980 | Furness et al. | 210/104 |
| 4,256,710 | 3/1981 | Azuma et al. | 422/5 |
| 4,345,996 | 8/1982 | Lindman et al. | 210/206 |
| 4,455,236 | 6/1984 | Kim | 210/721 |
| 4,719,088 | 1/1988 | Itoh et al. | 422/106 |
| 4,775,499 | 10/1988 | Hongo et al. | 261/106 |
| 4,844,874 | 7/1989 | deVries | 423/210 |
| 4,966,705 | 10/1990 | Jamieson et al. | 210/104 |
| 5,019,339 | 5/1991 | Keeney et al. | 422/5 |
| 5,032,287 | 7/1991 | Salmond | 210/737 |
| 5,122,165 | 6/1992 | Wang et al. | 55/38 |

Primary Examiner—Robert J. Warden
Assistant Examiner—Hien Tran
Attorney, Agent, or Firm—Sheridan, Ross & McIntosh

[57] ABSTRACT

A method and apparatus for treating nuisance odor streams is provided. One embodiment of the invention is directed to a method and apparatus in which deodorizing chemical agents are applied to an evaporative reaction pack situated within a gas chamber having an air stream running therethrough. The evaporative reaction pack provides a reaction zone within which the chemical agent is evaporated to facilitate a gas-gas or vapor phase interaction between the chemical agent and odoriferous compounds contained in the air stream. Another aspect of the present invention relates to a method and apparatus for batch processing of sewage within a wet well to prevent the formation of undesired compounds. In one embodiment, a predetermined amount of chemical agent, sufficient for treating the amount of sewage that the well can hold, is added to an evacuated wet well in coordination with the pumping of sewage from the wet well.

6 Claims, 6 Drawing Sheets

SEWAGE TREATMENT APPARATUS

FIELD OF THE INVENTION

The present invention relates generally to a method and apparatus for removing undesirable odorous compounds from air or gas streams and more particularly to a method and apparatus for reacting odoriferous compounds with vaporous deodorizing compounds within a reaction zone to remove odorous components from the air or gas stream. Another aspect of the present invention relates to a method and apparatus for conditioning sewage within a wet well to prevent the formation of undesired odorous compounds.

BACKGROUND OF THE INVENTION

The general objective in the treatment of gas streams from industrial and sewage plants is to remove from such gas streams odorous constituents, such as volatile organic compounds (VOCs) and volatile inorganic compounds (VICs). It is well known in the prior art to remove odors from waste gases in liquid-gas reactions through absorption utilizing spray towers systems and packed towers. In conventional spray tower systems, an aqueous solution containing one or more chemicals reactive toward an odorous contaminant is atomized to create liquid droplets which are dispersed into a gas stream. The atomized liquid droplets react with malodorous compounds to absorb odors and oxidation of such odors removes them from the gas stream. The reaction vessels are constructed to provide desired reaction times between the gas and the atomized aqueous/chemical fog, such reaction times typically ranging from about 5 to about 30 seconds or more for mist systems, and approximately 2 seconds for packed towers.

These and other traditional approaches have in common a relatively long contact time between gas and liquid, for mist scrubbers, and use a relatively large volume of liquid per volume of gas treated. Conventional spray and packed tower systems are inefficient with respect to the amount of chemical used. Moreover, conventional devices tend to be large and are expensive to construct and operate.

In other conventional liquid-gas absorption processes, packed tower systems are utilized to provide large surface areas for the liquid-gas reaction to occur. However, packings used in packed towers are often clogged by solid particulates and reaction products, negatively affecting the efficiency and overall function of such packed tower systems. Moreover, the size and expense of packed tower systems often precludes their use in many applications.

Problems in the treatment of sewage have also been encountered in the storage of sewage for extended periods of time. Among the problems, facultative bacteria present in sewage can react with sulfates in the absence of oxygen, thereby producing hydrogen sulfide, a malodorous poisonous gas, as well as other undesired odorous compounds. A combination of hydrogen sulfide gas with condensed water can form sulfuric acid which can cause deterioration of sewer pipes and sewer systems. Other undesirable compounds and gases may also form and need to be treated.

In conventional sewage systems, sewage is often held in various process apparatuses, such as a wet well, prior to treatment. Methods have been previously employed whereby chemicals are continuously fed into the wet well pump discharge line when the pump is operating or fed continually into the wet well. A continuous release system, however, may involve the undertreatment or overtreatment of sewage depending upon the time required for the wet well to fill to a predetermined level prior to evacuation. Alternatively, other systems treat malodorous sewage during the transport of such fluid from the wet well to other treatment containers. However, the sewage in the wet well prior to evacuation has the opportunity to ferment bacteria that produce undesired, odoriferous compounds.

SUMMARY OF THE INVENTION

One aspect of the present invention relates to a vapor phase deodorizing apparatus which effectively brings into contact an air or gas stream containing undesired odorous compounds with one or more volatile deodorizing compounds or chemical agents in a reaction zone so as to react the odorous compound with the deodorizing compound in an efficient gas-gas deodorizing reaction.

In one embodiment of the method invention, a volatile or vaporous deodorizing chemical is evaporated in a reaction zone through which a odoriferous containing air stream is passed through, thereby allowing a gas-gas reaction to occur. The vaporous deodorizing chemicals of the present invention can be any of a number of various odor counteractants and odor reactants. The deodorizing chemical is contacted with an evaporative reaction pack by means of a spray nozzle, such spray droplets of deodorizing chemical carried into the evaporative reaction pack by the air stream. The evaporative reaction pack into which the chemical spray is propelled and which receives the malodorous air stream and is designed so as to facilitate the evaporation of the chemical agents, reaction of the odorous compounds in the air or gas stream with the chemical agent. Liquid formed from the reacted malodorous compounds with deodorizing chemicals, as well as water accumulating within the evaporative reaction pack are removed from the reaction zone by gravity, forming drops of liquid which fall into the oncoming air stream and exit through a drain provided for in the gas reaction chamber.

An alternative embodiment of the invention utilizes a series of spray devices and evaporative reaction packs to, for example, treat the gas stream with several different chemicals.

Another embodiment employs an evaporative reaction pack downstream from the evaporative reaction pack or packs to remove moisture from the treated air stream.

Yet another embodiment of the apparatus employs two evaporative reaction packs, one oriented downstream from the spray device and the other oriented upstream and with one oriented above the other, to promote efficient use of the chemical. Specifically, chemical that does not react in the upper evaporative reaction pack can, once the pack becomes saturated, precipitate down onto the lower evaporative reaction pack where it has another opportunity to react with the malodorous gas stream and in essence pre-treat the gas stream.

Another aspect of the present invention involves the batch treatment of sewage stored in sewage storage vessels. In one embodiment of the invention, a predetermined amount of treatment chemical is added to a wet well, which directly receives raw sewage from, for example, one or more houses, after such wet well is evacuated or after such wet well contains sewage at some predetermined level. Untreated sewage enters the wet well and interacts with a predetermined amount of chemical until such wet well reaches a predetermined level. At such point, a pump is triggered which operates to evacuate the wet well to a force main or gravity main. When the wet well is sufficiently evacuated or at some predetermined level, the pump operation ceases, thereby allowing the wet well to refill with sewage. Upon the cessation of pumping and/or the substantial evacuation or attainment of a predetermined level in the wet well, a signal is conveyed to a chemical treatment reservoir to release another predetermined amount of treatment chemical sufficient to treat a predetermined volume of sewage in the wet well. As such, this embodiment of the present invention provides for an automatic, continuous batch feeding process and apparatus for treating sewage within a wet well or sewage storage vessel in a manner that provides for substantially equal treatment of all sewage passing through the wet well and prevents the formation of undesired odors or compounds without unduly wasting the treatment chemicals.

DETAILED DESCRIPTION OF THE INVENTION

The process and apparatus of the present invention may be understood by reference to the attached drawings. With respect to the apparatus shown in FIG. 1, an air or gas stream 10 containing odorous or otherwise undesired constituents is passed into a gas chamber 12 and passes through a bottom evaporative reaction pack 16 for removing at least a portion of an odoriferous constituent, continues to travel upwards through a top evaporative reaction pack 22 for further removing the malodorous component of the gas stream and exits to the environment. A "chemical agent", which can be any volatile substance capable of reacting with undesired compounds, and specifically, with odorous compounds, is contacted with the air stream 10 in the bottom evaporative reaction pack 16, top evaporative reaction pack 22 and the volume therebetween such that gas-gas or vapor phase reactions occur between the chemical agent and undesired odorous compound. Suitable chemical agents include odor counteractants such as those formulated from a blend of vegetable essential oils, and other reactants, such as NuTech's Chi-X Odor Eliminator, NuTralite Odor Eliminator, and DeAmine Odor Eliminator. The chemical agent can be carried in an aqueous solution, and preferably is present in a concentration of about 0.3% to about 10%.

Figure 1:
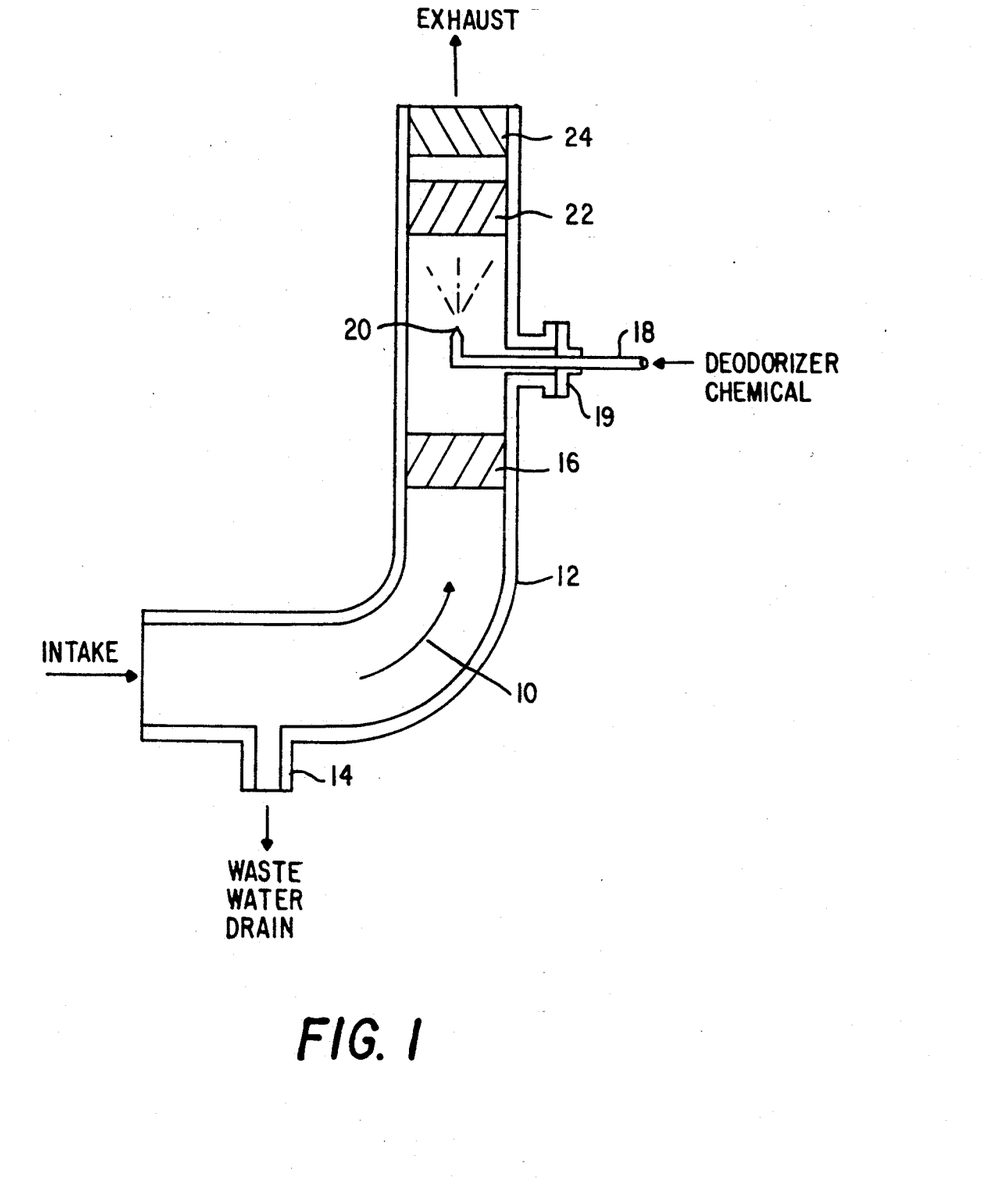
FIG. 1 is a schematic view of the deodorizing apparatus of the present invention.

While the aqueous chemical agent can be contacted with the bottom and top evaporative reaction packs 16, 22 in any effective manner, in the illustrated embodiment it is applied to the evaporative reaction packs by using a spray means such as a nozzle 20. Thus, in one embodiment a nozzle 20, connected to a pressurized chemical spray supply line 18, is provided in the interior of the gas chamber 12. A desired amount of chemical agent mixed with water is delivered through the chemical supply line 18 and exists from the nozzle 20 to create an atomized fog or mist within the gas chamber 12.

An appropriate nozzle is selected and the pressure of the chemical spray is adjusted to coincide with the air stream flow 10 so that a desired amount of chemical agent is carried by the air stream into contact with the top evaporative reaction pack 22. Typically, the top evaporative reaction pack 22 becomes saturated with the chemical agent and, in many situations, more agent is present than capable of reacting with the malodorous agent in the gas stream 10 in the top evaporative reaction pack 22. In this case, the unused chemical agent precipitates, along with the reacted chemical agent, and falls on the bottom evaporative reaction pack 16 where it can now react with the gas stream 10 and, in effect, act as a pre-treatment of the gas stream 10 that promotes efficient utilization of the chemical agent.

The nozzle 20 used to apply the spray in the illustrated embodiment of the present invention preferably generates droplets of less than 200 microns, more preferably between 20 and 100 microns and most preferably between 50 and 60 microns. The nozzle 20 can be modified dependent upon the intensity of odors encountered in a particular air stream 10. The preferred nozzle 20 for use in a system treating a 1000 cubic feet per minute air stream will handle approximately 0.6 gallons of chemical agent per hour. Preferably, the nozzle 20 is positioned with a specially designed bracket/flange assembly 19 so that the nozzle 20 is easily removable from the gas chamber 12 for cleaning and maintenance.

Figure 2A:
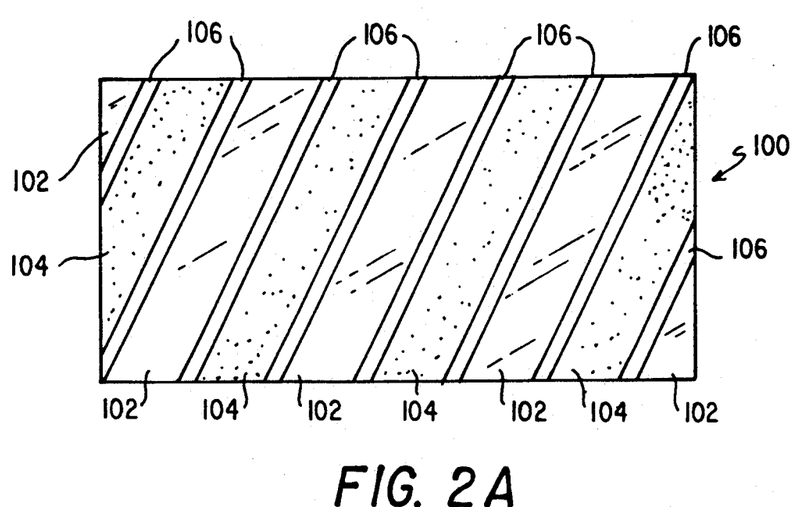
FIG. 2A is a side view of the evaporative reaction pack used in the present invention.
Figure 2B:
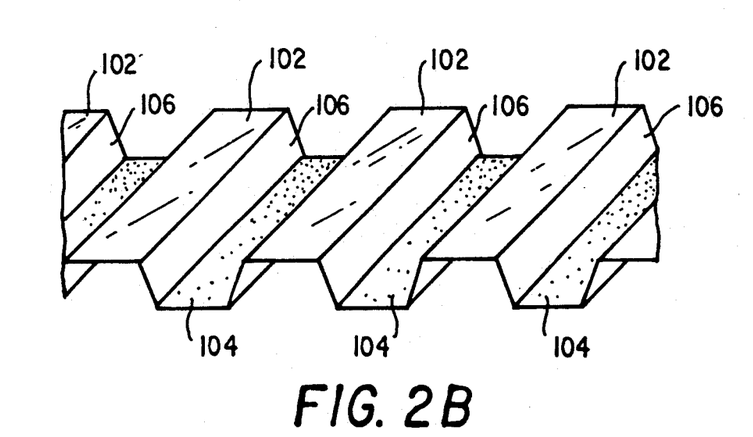
FIG. 2B is a perspective view of one layer of the evaporative reaction pack used in the present invention.

While the orientation of the nozzle 20 shown in FIGS. 1 and 2 is in the direction of the air stream 10, it is also within the scope of the present invention to have the nozzle 20 spraying in a direction counter to the air stream 10. It is, however, of primary importance that the chemical agent is sufficiently and effectively applied to at least one of the bottom and top evaporative reaction packs 16, 22 in a manner so as to facilitate the desired evaporation and gas-gas reaction of chemical agent with the odorous air stream. The spray pattern produced by the nozzle 20 should encompass the diameter of the gas chamber and evenly contact the bottom surface of the top evaporative reaction pack 22.

A fan (not shown) can be provided in communication with the gas chamber to increase the velocity of the air stream 10 to facilitate the carrying of chemical agent onto the top evaporative reaction pack 22 if needed.

The application of the sprayed chemical agent onto the bottom and top evaporative reaction packs 16, 22 creates a film on the surfaces within the evaporative reaction packs 16, 22. The numerous convoluted surfaces within the bottom and top evaporative reaction packs 16, 22 afford effective evaporative surfaces for the chemical agent that enhance the chemical reaction between the air stream 10 and the chemical agent. Odor components within the air stream 10 enter the bottom and top evaporative reaction packs 16, 22 and react with the evaporated chemical agents, thus generating a liquid which accumulates on the surfaces of the evaporative reaction packs 16, 22, precipitates, and eventually falls to the bottom of the vessel 12 where it leaves the vessel via drain 14.

In the illustrated embodiment of the invention a bottom evaporative reaction pack 16 is provided which acts to collect unreacted chemical agent that falls from the top evaporative reaction pack 22. The accumulation of such liquid eventually coats the interior surfaces of the bottom evaporative reaction pack 16 with the chemical agent. The presence of unreacted chemical agents in the bottom evaporative reaction pack 16 allows for the interaction of odoriferous compounds in the air stream 10 entering the bottom evaporative reaction pack 16 and, in effect, pre-treats the gas stream 10.

As described in greater detail below, the bottom and top evaporative reaction packs 16, 22 and the volume in between the packs provides a reaction zone where the incoming air stream 10 can react with the chemical agent. The convoluted construction of the bottom and top evaporative reaction packs 16, 22 facilitate the evaporation of chemical agent into a gas or vapor form to enable its reaction with odorous compounds in the air stream.

The top and bottom evaporative reaction packs 22, 16 are preferably of identical construction. In general, the evaporative reaction packs 22, 16 are positioned so as to completely extend across the diameter of the gas chamber 12 and are of a sufficient thickness (depth) to accommodate a particular range of air stream 10 flows. For example, each of the evaporative reaction packs 16, 22 have a depth of approximately four inches, which is sufficient to accommodate air streams 10 of between 500 and 1100 cubic feet per minute. Further, each of the evaporative reaction packs 16, 22 is preferably selected to be of sufficient depth to avoid, for a given air stream flow, having liquid carried through the pack. The evaporative reaction packs 16, 22 depths are therefore selected in order to accomplish the evaporation of chemical agents for reaction with the malodorous component of the air stream and the condensation of substantially all other liquid components in the air stream 10 so that no substantial amount of liquid exits the pack with the exiting air stream 10. If, however, an undesirable amount of liquid is present in the exiting air stream, a demister 24 can be placed downstream relative to the direction of air flow to facilitate the condensation of such liquids.

A suitable evaporative reaction pack provides a chamber for facilitating or enhancing reaction between the chemical agent and the gas stream 10 by promoting evaporation of chemical agents so that the desired gas-gas or vapor phase reaction can occur between the chemical agent and the air stream. The evaporative reaction packs 16, 22 each essentially form a reaction zone in which evaporation of the chemical agent is facilitated and reaction between the gaseous chemical agent can then occur with odoriferous compounds contained in the air stream 10. Specifically, the preferred packs 16, 22 promote substantially even distribution of air, as well as deodorizing chemical carried therein, over substantially the entire surface area of the packs.

As a result, atomized droplets of aqueous chemical agents carried in the air stream 10 are substantially evenly distributed over the surfaces within the evaporative reaction pack 22.

The evaporative reaction pack is preferably constructed to permit the multiple channeling of the incoming air stream 10 through the reaction zone with little loss of air pressure, while simultaneously facilitating the contact of incoming air with numerous other channeled air streams within the reaction zone. Within the reaction zone, air streams are directed so as to collide with other air streams, providing circulating eddies of air currents and other accelerated air current within the reaction zone. The air channel intersections create miniature centrifugal separators or vortices that accelerate the air stream passing through the reaction zone. Such air movement through the reaction zone facilitates the evaporation of chemical agent from the aqueous solution and thereby allows a gas-gas or vapor phase reaction to occur between the odoriferous compounds in the air stream and the chemical agent. Air channels are therefore provided with different angles throughout the reaction zone to create vortices and intersections which facilitate the separation of both odorous components from the air stream 10, as well as chemical deodorizing agents from the liquid spray, as the air stream 10 passes through the evaporative reaction pack 16, 22.

Figure 3:
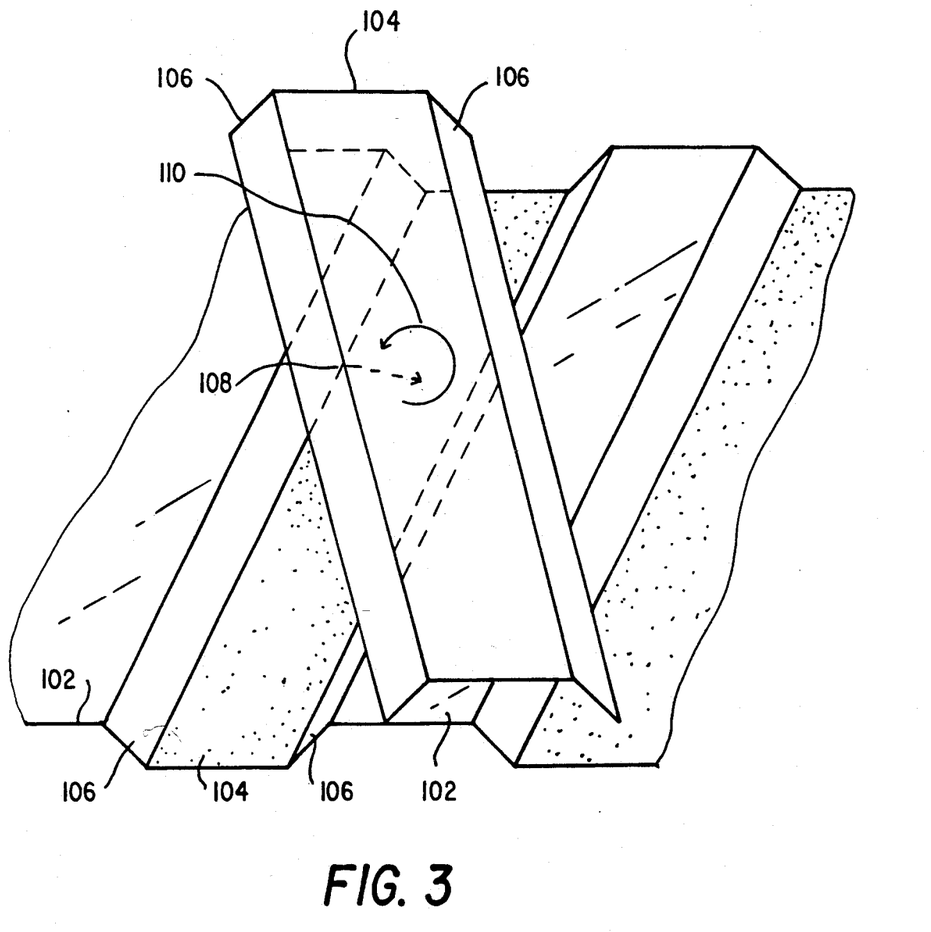
FIG. 3 is a perspective view of the two layers evaporative reaction pack that illustrates the vortex producing intersection of the channels associated with the two layers.

A suitable evaporative reaction pack can be obtained from Brentwood Industries, located in Reading, Pa., such evaporative reaction pack having a three-eights inch convoluted cross-flow packing structure that is illustrated in FIGS. 2A, 2B, and 3. A single layer 100 of the evaporative reaction pack is illustrated in FIGS. 2A and 2B. The layer 100 includes mesas 102 that are separated from channels 104 by sloping side members 106. The mesas 102, channels 104, and sloping side members 106 all run at an angle of approximately 60°. As illustrated in FIG. 3, an evaporative reaction pack is realized by juxtaposing two or more of the layers 100 such that the channels 104 of adjacent layers cross or intersect at point 108. The intersecting channels, it was discovered, produced vortices 110, when an air or gas stream is passed through the pack. As a result, when the air stream 10 which is carrying the chemical agent enters a pack, the resulting vortices created by the pack distribute the chemical agent over the surfaces of the pack for evaporation and promote the reaction between the gas and the evaporated chemical agent by forcing them into intimate contact with one another.

In a preferred embodiment, the evaporative reaction pack 16, 22 is designed in a convoluted structure having numerous vortices therein so that the air stream 10 entering the evaporative reaction pack 16, 22 is channelled and accelerated around and between sharply converging surfaces within the evaporative reaction pack. The design of the evaporative reaction pack 16, 22 thus facilitates the mixing of air from various channels within the evaporative reaction pack 16, 22, achieving an even distribution of air through the evaporative reaction pack 16, 22, significant mixing of the air stream 10 within the reaction zone, and substantial surface contact of the air stream 10 with the evaporative reaction pack.

The evaporative reaction packs 16, 22 of the present invention do not significantly slow down the air stream flow 10 and do not create a high pressure drop in the gas chamber. In one embodiment, the pressure drop through a four inch evaporative reaction pack is only about one-quarter to three-eights of an inch. As a result, the apparatus can be operated in a cost-effective manner because little energy needs to be expended in overcoming the apparatus's resistance to air flow. Stated another way, the apparatus exhibits little resistance to air flow.

A preferred pack will allow a particular air flow channel in such evaporative reaction pack 16, 22 to cross with other air flow channels about five to eight times in a depth of about four inches.

In a preferred embodiment of the invention, the detention time of chemical agents and odoriferous compounds within the air stream is approximately one third of a second, compared with between two to twenty seconds of detention time in conventional mist tower and packed tower devices.

The air stream passing through the reaction zone should be of sufficient velocity to carry the chemical deodorizing agent into, but not completely through, the evaporative reaction pack to effect desired evaporation of chemical agents. Upon evaporation, the deodorizing chemical vapor is able to react with malodorous compounds and to coalesce on the surface of the evaporative reaction pack, ultimately forming drops that fall from the reaction zone through a drain or air inlet at a lower portion of the apparatus. To promote efficient utilization of the chemical agent, a series of fixed media evaporative reaction packs can be situated in the contact gas chamber.

Depending upon the volume of air stream 10 to be treated and the intensity of odors encountered, a suitable evaporative reaction pack 16, 22 is selected of appropriate depth and size to facilitate the effective evaporation of chemical agent and reaction with odorous compounds in such air stream 10. In one embodiment, the evaporative reaction pack 16, 22 preferably has sufficient cross-sectional area and depth sufficient to treat both low and high odor intensity air streams 10 having volumes of up to 15,000 cubic feet per minute.

In one embodiment, the evaporative reaction pack 22 is positioned within the gas chamber 12 a sufficient distance from the spray nozzle 20 so as to enhance a substantially even distribution of the liquid spray across the extent of the evaporative reaction pack 22 structure. The efficiency of the apparatus depends, to some extent, on a balance of air stream 10 velocities, spray nozzle 20 droplet size and spray application, together with the configuration and proximity of the evaporative reaction pack 16, 22. For example, if the volume of air within a gas chamber is too great, or alternatively if the depth of the evaporative reaction pack 16, 22 is too small, then an insufficient reaction zone will be created and liquid containing chemical agent therein may be transported through the evaporative reaction pack 22 with the air stream 10 without achieving desired evaporation and reaction with odor compounds.

In one embodiment of the present invention, approximately one gallon of water/deodorizing chemical per hour is utilized. This is more efficient than known conventional liquid-gas devices that typically utilize from one to over ten gallons per minute of liquid to treat similar volumes of air. The superior efficiency of the present invention is believed to be principally due to the improved vapor phase reaction of malodorous compounds with gaseous deodorizing chemical agents achieved by the apparatus.

Figure 4:
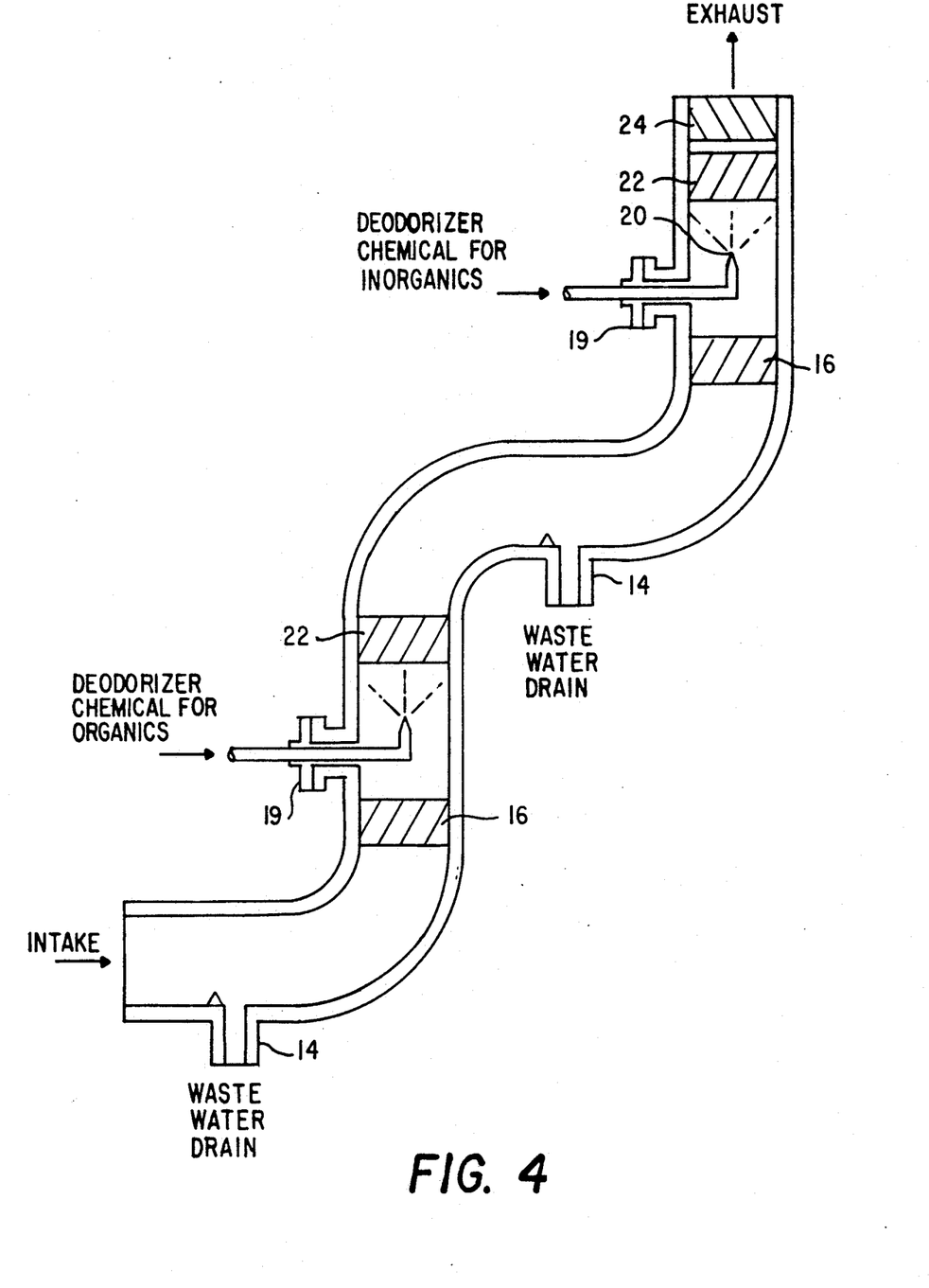
FIG. 4 is a schematic view of the present invention showing the ability to connect individual apparatuses in series to accommodate different or supplemental deodorizing treatments.

While only one nozzle 20 is shown in FIG. 1, it is to be understood that a plurality of such nozzles 20 can be employed depending upon the volume of air stream 10 to be treated. Moreover, arrangement of more than one apparatus of the present invention within an air stream, as shown in FIG. 4, can be employed to treat various types of odoriferous components contained such air stream 10. For instance, a gas chamber 12 may be fitted with several stages of evaporative reaction packs 16, 22 and nozzles 20, each nozzle 20 capable of providing a distinct chemical reactant spray. Such an arrangement therefore allows for the treatment of an air stream 10 having multiple contaminants therein.

In comparison with conventional liquid-gas treatment devices, the present invention provides for a compact, relatively inexpensive unit to make and operate that is able to effectively remove odorous compounds from air streams 10. Traditional packed tower devices, for treating 1000 cfm, for example, typically include scrubbers of twelve to eighteen inches in diameter and that are over twenty feet in length, containing approximately ten feet of packing material. In comparison, the present invention can be used in conventional twelve inch diameter gas chambers and are generally less than six feet in length. The present system is therefore capable of being easily retrofitted in existing foul air ventilation systems. In comparison with packed tower structures, considerable cost savings are achieved due to the elimination of the costly packed media that do not redirect the air flow of the air stream in a manner so as to achieve the evaporative function facilitating the gas-gas reaction of the present invention.

The present invention has reduced the energy requirements over both conventional spray tower systems and packed tower systems. Spray tower systems, while having relatively low pressure drops (i.e., about ½ inch) require significant energy to power an air compressor required to generate the pressurized, atomized liquid sprays used in such systems. Packed towers typically have substantial pressure drops of up to three inches and therefore require significantly more energy to generate desired air stream velocities. Moreover, in the present invention application of chemical agents to the air stream 10 can be performed without the use of compressed air since only pressure atomization of a chemical agent is required. Using the evaporative reaction pack entrainment system of the present invention, lower chemical costs are encountered due to the increased efficiency of the reaction of the chemical agent with the air stream 10.

Figure 5:
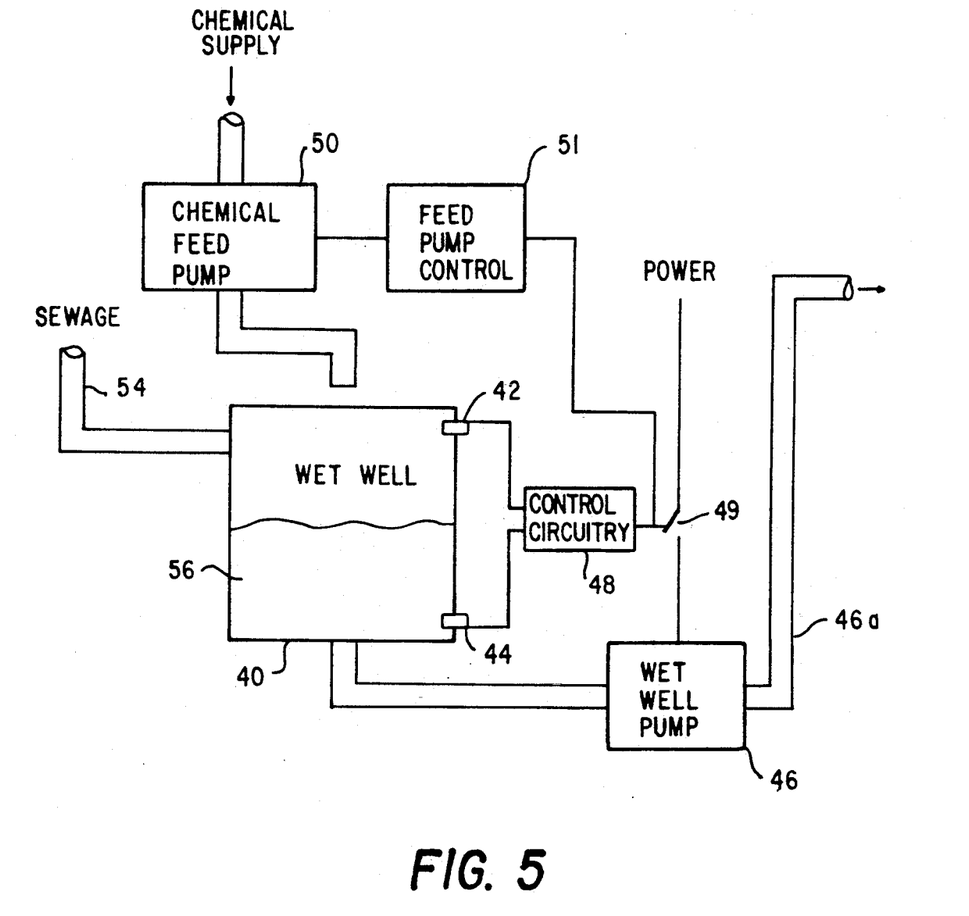
FIG. 5 is a schematic diagram of one embodiment of the invention in which a predetermined amount of chemical agent can be released into a wet well or other storage vessel upon receiving a signal from a feed pump control.

Referring now to FIG. 5, a separate embodiment of the present invention relates to a system for automatic batch feeding of a predetermined amount of sewage treatment chemical into a sewage containment vessel, such as a wet well, when there is a predetermined amount of sewage in the vessel.

Typically, a wet well 40 is connected to a pump 46 which operates to evacuate the wet well 40 when a particular amount or level of sewage is deposited therein via a sewage line 54. More specifically, when sewage has filled the wet well 40 or is at some predetermined level therein, a first transducer 42 generates a signal that is provided to control circuitry 48 which closes switch 49, thereby providing power to the pump 46. The pump 46 then evacuates sewage from the wet well 40 to allow room for further sewage and to transfer the accumulated sewage via what are typically referred to as force mains or gravity mains 46a for further treatment or disposal. At a point when the wet well 40 is substantially evacuated, the pump is shut off so as to allow the wet well 40 to once again fill with sewage.

More specifically, a second transducer 44 senses when the wet well 40 has been evacuated or there is a predetermined amount of sewage contained therein and generates a signal that is provided to the control circuitry 48. In response, the control circuitry 48 opens switch 49 to turn off the pump 46. The filling up and evacuation of a typical wet well often occurs at different rates depending upon the time of day. For example, a wet well in a housing subdivision may go through a fill up-/evacuation cycle eight to ten times an hour during morning hours when a significant number of people are performing their morning ablutions, but only once during the mid-day when most of these people are away at work.

One aspect of the present invention relates to the treatment of a given amount of sewage 56 in the wet well 40 with a sufficient amount of chemical agent to adequately prevent the formation of undesired compounds, such as hydrogen sulfide. To do so, the volume of the wet well 40 is determined and a volume of chemical agent is calculated for treating such volume of sewage. Upon the evacuation of the wet well 40 and the cessation of sewage pumping therefrom, the signal used to open switch 49 is also conveyed to a feed pump control unit 51 which operates to trigger the chemical feed pump 50 to release a predetermined amount of chemical into the wet well 40 within a predetermined amount of time, typically less than one minute. As sewage 56 then accumulates in the wet well 40, it mixes and reacts with the added chemicals to prevent the production of undesired compounds and odors. The incoming sewage mixes with the added chemicals until the high level mark on the wet well is again reached and the pump 46 is again activated to evacuate the wet well 40. In such a manner, batch processing of sewage in the wet well 40 is accomplished that makes efficient use of the treatment chemical and prevents the formation of undesirable compounds that may pose a health hazard as well as possibly damaging the sewage system.

Figure 6:
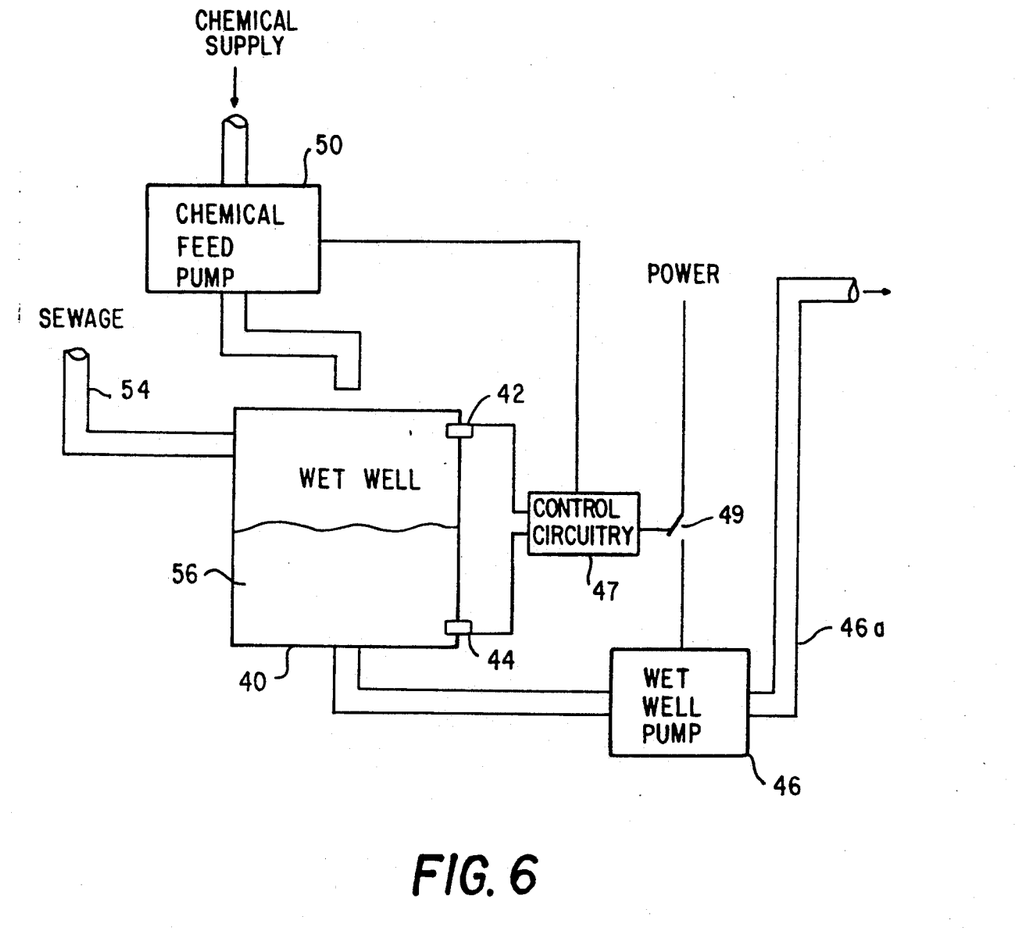
FIG. 6 is an alternate embodiment of the invention illustrated in FIG. 5.

To summarize the operation of the illustrated embodiment, the control circuitry 48 is activated by the first transducer 42 when the amount of sewage 56 reaches a certain high level point within the wet well 40. At such high sewage level the control circuitry 48 in turn sends a signal which activates the wet well pump 46 to evacuate the accumulated sewage 56. At a low level point when sewage 56 is substantially evacuated from the wet well 40 the control circuitry 48 is triggered by the second transducer 44 to shut off the pump 46. Upon a signal being transmitted by the control circuitry 48 to cause cessation of pumping of sewage 56 from the wet well, and/or upon a signal being transmitted to the control circuitry 48 when the second transducer 44 is triggered by a low sewage level, the feed pump control 51 is activated to cause the chemical feed pump 50 to dose the wet well with an amount of chemical based upon the volumetric capacity of the evacuated wet well 46. The feed pump control 51 and the control circuitry 48 can be combined into one unit as illustrated in FIG. 6 and housed in lockable, corrosion resistant, weatherproof boxes fitted with mounting brackets for easy installation to wet well facilities. The present invention thus allows for the use of a compact, inexpensive chemical feed system which prevents the odor problems and corrosive problems encountered in conventional sewage treatment systems.

Alternative embodiments of the present invention include directly connecting the first and second transducers 42, 44 to a feed pump control that is adapted to process the signals provided by the transducers. Further, the chemical feed pump 50 can be triggered when the wet well 40 is partially filled with sewage, if so desired. Other embodiments include the programming of the control assembly 47 to trigger the evacuation of the wet well 40 and to discharge a predetermined amount of chemical into the wet well 40 at desired times of day or after predetermined sewage holding times. Automatic operation of the system may be achieved by installing into the various flow lines control items capable of monitoring and controlling various functions and cycles of the system. Hydraulic and atmospheric pressure switches may be used to control liquid levels and timer operated switches may be employed to achieve a self-sustaining continuous automatic operation.

The chemical agents used in the present invention are preferably able to complex with hydrogen sulfide or otherwise act to prevent bacterial generation of undesired compounds. The chemical deodorizing agents suitable for use in the present invention include, but are not limited to, chemical agents reactive with odorous compounds including those associated with fecal matter such as the indoles and skatoles, and sulfur containing compounds including mercaptans and sulfides, and particularly hydrogen sulfide. Preferably, the following chemical agents are used: Pond X2 ™ Odor Eliminator and Sulfaway $H_2S$ Scavenger. Traditional iron salt, nitrates and oxidant chemical feed can also be utilized with the present invention.

Further, should it be desirable, the deodorizing invention illustrated in FIG. 1 can be used to treat odorous gases emanating from the sewage storage vessel or wet well or coming off of the forced line.

While various embodiments of the present invention have been described in detail, it is apparent that modifications and adaptions of those embodiments will occur to those skilled in the art. It is to be expressly understood, however, that such modifications and adaptions are within the scope of the present invention, as set forth in the following claims.

What is claimed is:

1. An apparatus for treating sewage in a wet well that has a defined volume and is occasionally pumped out by a wet well pump, comprising:
    means for sensing when a wet well is substantially empty and generating an output signal upon sensing when said wet well is substantially empty; and
    means, responsive to said output signal, for discharging a sewage treatment chemical into the substantially empty wet well, wherein sewage entering the wet well mixes with said sewage treatment chemical and substantially immediately begin reacting with said sewage treatment chemical to inhibit an undesirable chemical in the sewage.

2. An apparatus, as claimed in claim 1, wherein:
    said means for sensing and generating includes means for interfacing with a wet well pump controller that activates a wet well pump to evacuate sewage from the wet well when a defined volume of sewage is detected in the wet well and to deactivate the wet well pump when the wet well is substantially empty.

3. An apparatus, as claimed in claim 1, wherein:
    said means for discharging sewage treatment chemical includes means for discharging a predetermined amount of sewage treatment chemical necessary to substantially inhibit the undesirable chemical in the volume of the sewage contained in a wet well when the wet well is at level at which the wet well is to be pumped out by a wet well pump.

4. An apparatus for treating sewage in a wet well that contains a defined volume of sewage and is occasionally pumped out by a wet well pump comprising;
- means for sensing when a wet well is substantially empty and generating an output signal upon sensing when a wet well is substantially empty;
- means, responsive to said output signal, for discharging an amount of sewage treatment chemical into the substantially empty wet well that is sufficient to substantially inhibit an undesirable chemical in the defined volume of sewage, wherein sewage entering the wet well mixes with said sewage treatment chemical and substantially immediately begin reacting with said sewage treatment chemical to inhibit the undesirable chemical in the sewage.

5. An apparatus, as claimed in claim 4, wherein:
- said means for sensing and generating includes means for interfacing with a wet well pump controller that activates a wet well pump to evacuate sewage from the wet well when a defined volume of sewage is detected in the wet well and to deactivate the wet well pump when the wet well is substantially empty.

6. An apparatus for treating sewage comprising:
- a wet well for containing a defined volume of sewage and being located to receive raw sewage;
- a wet well pump for removing sewage from said wet well;
- first means for detecting a first predetermined level of sewage in said wet well and generating a first output signal upon detecting said first predetermined level, wherein said first predetermined level is a level at which said wet well contains said defined volume of sewage;
- second means for detecting a second predetermined level of sewage in said wet well and generating a second output signal upon detecting said second predetermined level, wherein said second predetermined level is a level at which said wet well is substantially empty;
- first control means, responsive to said first output signal and said second output signal, for activating and deactivating said wet well pump, wherein said first control means activates said wet well pump to pump sewage out of said wet well upon receipt of said first output signal and deactivates said wet well pump upon receipt of said second output signal;
- second control means, located so as to receive said second output signal produced by said second means for detecting and indicative of said wet well being substantially empty, for generating a third output signal in response to said second output signal; and
- means, responsive to said third output signal, for dispensing a predetermined amount of sewage treatment chemical into a substantially empty wet well to substantially inhibit an undesirable chemical in the sewage, wherein said sewage treatment chemical, after being dispensed into said substantially empty wet well, mixes with sewage upon the entry of sewage into said wet well, and said sewage treatment chemical substantially immediately begins reacting with sewage entering said wet well to inhibit said undesirable chemical in the sewage, and said predetermined amount of sewage treatment chemical is sufficient to inhibit said undesirable chemical in said defined volume of sewage and thereby make efficient use of said sewage treatment chemical.

* * * * *